Sept. 9, 1952 C. M. AMLING ET AL Plant Pat. 1,126
ROSE PLANT
Filed Sept. 11, 1951
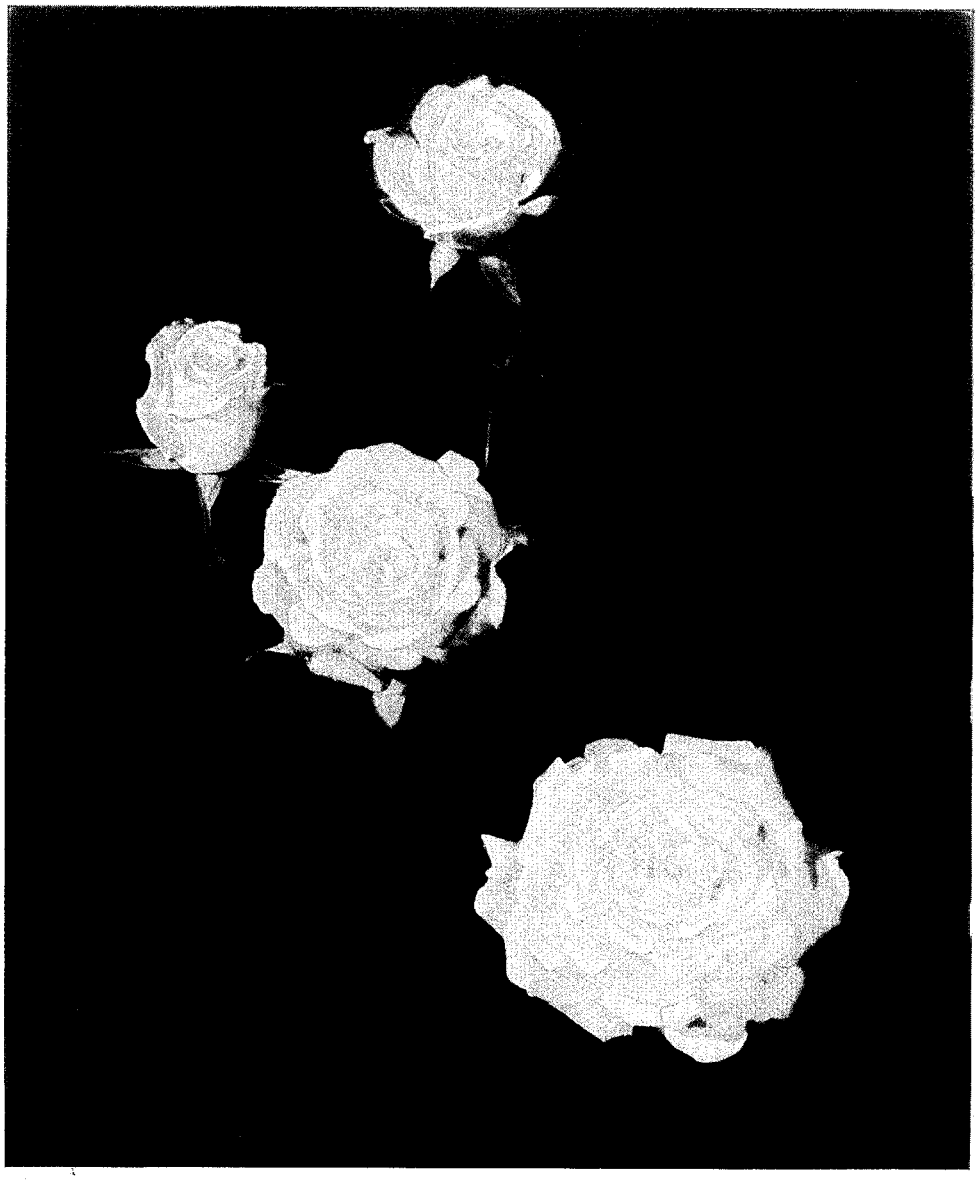
INVENTOR
Clarence M. Amling & Gabriel Beltran
By Orville M. Kile
Plant Patent Agt.

Patented Sept. 9, 1952

Plant Pat. 1,126

UNITED STATES PATENT OFFICE 1,126

ROSE PLANT

Clarence M. Amling and Gabriel Beltran, Santa Ana, Calif., assignors to Clarence Amling Roses, Inc., Santa Ana, Calif.

Application September 11, 1951, Serial No. 246,024

1 Claim. (Cl. 47—61)

Our present discovery relates to a new variety of polyantha rose plant, its most distinguishing feature being the color and size of its flower in this class of roses. The new variety originated as a sport of the variety Garnette (unpatented) and was discovered by us in our greenhouses in Southern California. Asexual reproduction by means of budding has been accomplished by us at the same location, and the distinguishing features appear to be permanent.

This new variety is similar to its parent in some respects but differs principally because of its consistently larger flowers of better keeping qualities and a widely different color from that of the flowers of the parent variety.

The variety known to us which is most like our new variety is Pink Garnette (unpatented) but it is a much lighter pink color which falls about half way between the color of Pink Garnette and Demure (unpatented) which is a very delicate pink. Also, the flowers of our variety are consistently larger than those of the two above-mentioned varieties, both in the bud stage and when fully expanded, and usually have a larger number of petals. The bud of our new variety is longer than that of either of these other varieties. As compared with these two varieties, the growth of our new variety is a bit more vigorous and sturdy.

Illustrations accompanying this specification are color photographs of four specimens of the flower of this variety in different stages of opening, together with portions of stems and foliage. The flowers and steams are shown in approximately their true coloring. Foliage, however, is somewhat darker than the natural foliage, which is frequent in color photography. However, no claim is made that the foliage color differs from that of the parent variety.

In the following detailed description, any reference to color plates indicates Ridgway's Color Standards and Nomenclature. Other color references indicate the usual dictionary meaning.

*The plant*

Growth: Bushy. Very vigorous and sturdy, growing to 4 or 5 feet in height. Breaks readily and freely.

Blooming habit: Continuous bloomer the year around. Very prolific.

Borne: Singly and in clusters.

Stems:

*Color.*—Approximately Grass Green (Plate VI).

*Strengths.*—Very strong and upright.

*Type.*—Zigzagged, with short internodes.

*Thorns.*—None appear on upper portion of stems but numerous large, sharp thorns are found on lower part of stem. These are downward pointing, greenish colored, and staggered in their position on the stem.

Foliage:

*Leaves.*—Mostly 3 to 7 leaflets with terminal three much larger than the others. Leaves nearest flower are often single, narrow appendages similar to the sepals.

*Size.*—Terminal leaflets are usually 2½ to 3½ inches long by 1½ to 2¼ inches wide.

*Shape.*—Oval, with acute to acuminate apex. Base sometimes rounded. Edges deeply and sharply serrated.

*Texture.*—Leathery.

*Color.*—Upper surface dark, shiny green, approximately Elm Green (Plate XVII).

*Rachis.*—Slender; grooved above; occasional small thorn underneath.

*Stipules.*—Clinging; small.

*Disease resistance.*—Very healthy and apparently free of diseases common to roses.

*The flower*

Bud:

*Size.*—Medium, approximately 1½ inches long.

*Shape.*—Longer than buds of most similar varieties. Pointed when small.

*Sepals.*—Rather long but mostly simple with a few small side appendages. A few are foliaceous.

*Peduncle.*—Short, straight and strong.

*Opening.*—Opens evenly.

Bloom:

*Size.*—Medium. Best specimens are 2½ to 3 inches in diameter when fully expanded.

*Form.*—Full, with depressed center at first, later opening with flat top because of shorter inner petals. Outer and intermediate petals reflex slightly and the full center spreads but stamens are seldom visible until the very late stages of opening.

*Petalage.*—Very double. Number of petals varies from around 60 to 90, usually in excess of 70, including small petals in center.

*Longevity.*—Flower lasts well both on the bush and when cut.

*Fragrance.*—Abundant and pleasing.

*Color.*—Deep in the center of the opening bloom, the color is Deep Rose Pink (Plate XII) or a little darker. The outer five or six rows of petals are much lighter and in the stage when the stamens are visible the outer petals are approximately Rose Pink (Plate XII). Petals are about the same color on both surfaces except for the outer row which is usually lighter on the reverse surface, particularly at the base which contains considerable greenish white in its coloring.

Petals:

*Size.*—Outer petals average about 1¼ inches long and slightly narrower. Inner petals are substantially smaller.

*Shape.*—Obcordate. Edge frequently somewhat wavy and slightly notched. Inner petals are of course much more spatulate.

*Appearance and texture.*—Substantial but soft and silky.

*Arrangement.*—Imbricated and slightly reflexed.

*Persistence.*—Cling well.

Reproductive organs:

*Pistils.*—Many, bunched in center of flowers. *Styles*—slender, white and uneven. *Stigmas*—greenish white.

*Stamens.*—Surround pistils. *Filaments*—irregular in length. *Anthers*—medium size.

*Pollen.*—Plentiful; golden yellow.

Having thus disclosed our discovery, we claim:

The new and distinct variety of polyantha rose plant similar in many respects to its parent but characterized as to novelty particularly by its very vigorous and abundant growth; its prolific and continuous blooming habit; and its relatively larger and longer buds and larger flowers of rose pink as shown and described.

CLARENCE M. AMLING.
GABRIEL BELTRAN.

No references cited.